(12) United States Patent
Stark et al.

US008871462B2

(10) Patent No.: US 8,871,462 B2
(45) Date of Patent: Oct. 28, 2014

(54) SCAFFOLD-BASED ORGANOTYPIC CULTURE FOR THE LONG-TERM CULTIVATION OF HUMAN EPIDERMAL STEM CELLS

(75) Inventors: Hans-Juergen Stark, Meckesheim (DE); Norbert Fusenig, Heidelberg (DE); Petra Boukamp, Happenheim (DE); Karsten Boehnke, Heidelberg (DE)

(73) Assignees: Deutsches Krebsforschungszentrum, Heidelberg (DE); Landesstiftung Baden-Wurttemberg gGmbH, Stuttgart (DE)

( * ) Notice: Subject to any disclaimer, the term of this patent is extended or adjusted under 35 U.S.C. 154(b) by 0 days.

(21) Appl. No.: 13/636,122

(22) PCT Filed: Mar. 22, 2011

(86) PCT No.: PCT/EP2011/054337
§ 371 (c)(1),
(2), (4) Date: Nov. 27, 2012

(87) PCT Pub. No.: WO2011/117233
PCT Pub. Date: Sep. 29, 2011

(65) Prior Publication Data
US 2013/0078666 A1 Mar. 28, 2013

(30) Foreign Application Priority Data
Mar. 24, 2010 (EP) ..................................... 10157471

(51) Int. Cl.
*C12Q 1/02* (2006.01)
*C12N 5/071* (2010.01)
(52) U.S. Cl.
CPC ............ *C12Q 1/025* (2013.01); *C12N 2501/39* (2013.01); *C12N 2501/70* (2013.01); *C12N 2500/38* (2013.01); *C12N 2501/01* (2013.01); *C12N 2502/094* (2013.01); *C12N 2533/30* (2013.01); *C12N 2502/1323* (2013.01); *C12N 5/0698* (2013.01); *C12N 2533/56* (2013.01); *C12N 2501/15* (2013.01)
USPC ............................................. 435/29; 435/395
(58) Field of Classification Search
None
See application file for complete search history.

(56) References Cited

FOREIGN PATENT DOCUMENTS

EP 1918365 A1 * 5/2008
WO WO 2008/052963 A1 5/2008

OTHER PUBLICATIONS

Sun et al. "Culture of skin cells in 3D rather than 2D improves their ability to survive exposure to cytotoxic agents", Journal of Biotechnology 122: 371-381, 2006.*
Ma et al. "Potential of nanofiber matrix as tissue-engineering scaffolds", Tissue Engineering 11(1/2): 101-9, 2005.*
Sun et al. "Self-organization of skin cells in three-dimensional electrospun polystyrene scaffolds", Tissue Engineering 11 (7/8): 1023-1033, 2005.*
Kim et al. "Structural studies of electrospun cellulose nanofibers", Polymer 47: 5097-5107, 2006.*
International Preliminary Report on Patentability issued in related International Patent Application No. PCT/EP2011/054337, dated Oct. 4, 2012.
International Search Report issued in related International Patent Application No. PCT/EP2011/054337, completed May 12, 2011.
Written Opinion issued in related International Patent Application No. PCT/EP2011/054337, completed May 12, 2011.
Sun et al., "Development of a Bioreactor for Evaluating Novel Nerve Conduits," *Biotechnology and Bioengineering*, vol. 99, No. 5, pp. 1250-1260 (2008).
Sun et al., "Development of a Closed Bioreactor System for Culture of Tissue-Engineered Skin at an Air-Liquid Interface," *Tissue Engineering*, vol. 11, No. 11/12, pp. 1824-1831 (2005).
Sun et al., "Investigation of Fibroblast and Keratinocyte Cell-Scaffold Interactions Using a Novel 3D Cell culture System," *J. Mater Sci: Mater Med.*, vol. 18, pp. 321-328 (2007).
Slivka et al., "characterization, Barrier Function, and Drug Metabolism of an In Vitro Skin Model," *The Journ. of Investigative Dermatology*, vol. 100, No. 1, pp. 40-46 (1993).
Muffler et al., "A Stable Niche Supports Long-Term Maintenance of Human Epidermal Stem Cells in Organotypic Cultures," *Stem Cells*, 23 pages (2008).
Black et al., "In vitro Reconstruction of a Human Capillary-like Network in a Tissue-Engineered Skin Equivalent," *The FASEB Journal*, vol. 12, pp. 1331-1340 (1998).
Auxenfans et al., "Evolution of three dimensional skin equivalent models reconstructed in vitro by tissue engineering," *Eur. J. Dermatol.*, vol. 19, No. 2, pp. 107-113 (2009).
Auger et al., "Tissue-engineered skin substitutes: from in vitro constructs to in vivo applications," *Biotechnol. Appl. Biochem*, vol. 39, pp. 263-275 (2004).

* cited by examiner (Continued)

*Primary Examiner* — Ruth Davis
*Assistant Examiner* — Emily Cordas
(74) *Attorney, Agent, or Firm* — Foley & Lardner LLP

(57) ABSTRACT

The present invention relates to organotypic cultures of epidermal cells and the use thereof for the screening of pharmaceutical and cosmetic agents. Specifically, means for the improvement of the long-term stability of such cultures are disclosed. Thus, the present invention contemplates a skin equivalent comprising (a) a dermal equivalent comprising a matrix comprising nonwoven viscose fabric and fibroblasts and (b) keratinocytes. Moreover, the present invention contemplates a method for manufacturing the skin equivalent and a method for screening agents capable of influencing skin, such as a therapeutic or cosmetic agent.

11 Claims, 2 Drawing Sheets

(56) References Cited

OTHER PUBLICATIONS

Figure 1:
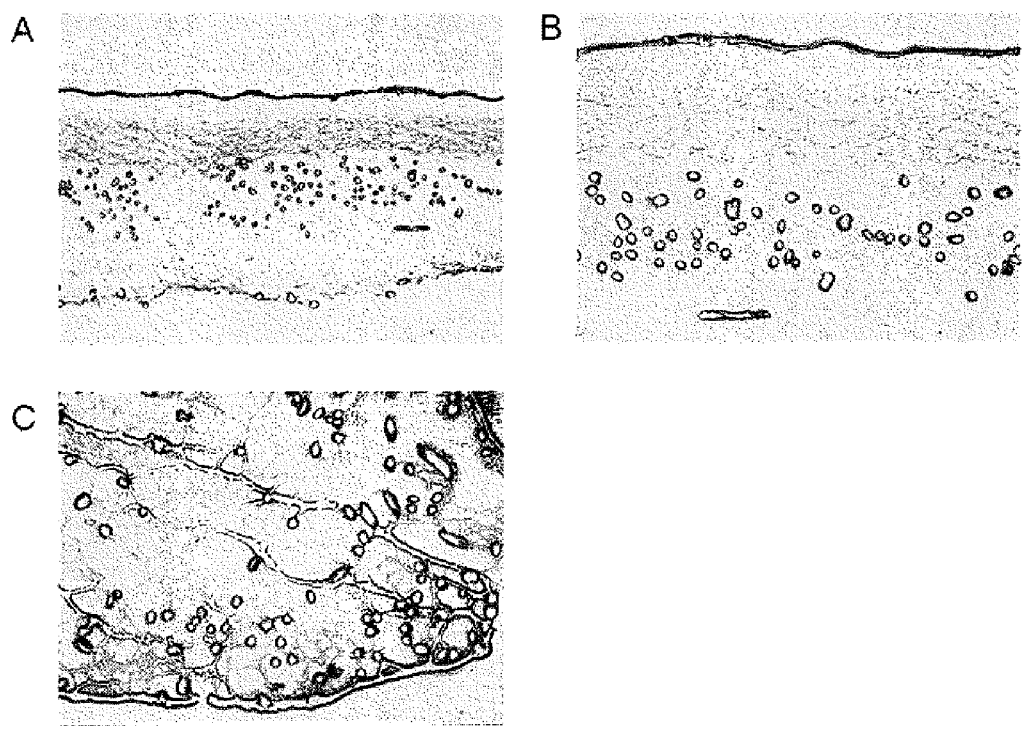

Carlson et al., "Three-Dimensional Tissue Models of Normal and Diseased Skin," *Current Protocols in Cell Biology*, pp. 19.9.1-19.9.17 (2008).

ISO 9073-1, First Edition, Textiles—Test Methods for nonwovens—Part 1: Determination of mass per unit area, Jul. 1, 1989, 8 pages.

ISO 9073-2, Second Edition, Textiles—Test Methods for nonwovens—Part 2: Determination of thickness, Dec. 1, 1998, 13 pages.

ISO 9073-3, First Edition, Textiles—Test methods for nonwovens—Part 3: Determination of tensile strength and elongation, Jul. 1, 1989, 8 pages.

Jean-Michel Anspach, EDANA, Standard Test Methods for the Nonwovens and Related Industries, Worldside Strategic Partners, "Harmonized Test Methods for the Nonwovens and Related Industries," Apr. 2011.

SCAFFOLD-BASED ORGANOTYPIC CULTURE FOR THE LONG-TERM CULTIVATION OF HUMAN EPIDERMAL STEM CELLS

The present invention relates to organotypic cultures of epidermal cells and their uses for the screening of pharmaceutical and cosmetic agents. Specifically, means for the improvement of the long-term stability of said cultures are disclosed. Thus, the present invention contemplates a skin equivalent comprising (a) a dermal equivalent comprising a matrix comprising (i) nonwoven viscose fabric and (ii) fibroblasts and (b) keratinocytes. Moreover, the present invention contemplates a method for manufacturing said skin equivalent and a method for screening of agents capable of influencing skin, such as a therapeutic or cosmetic agent.

The human skin does not only protect the human body from the external world, but it is also a target of many kinds of infectious and non-infectious diseases, such as skin cancer, wounds or acne.

The skin is composed of the so-called epidermis, an external epithelial component, and the so-called dermis, the underlying connective tissue component. The epidermis itself is primarily composed of keratinocytes which are arranged in stratified layers. The so-called stratum basale at the dermal-epidermal junction is a single layer of keratinocytes with a small number of interspersed melanocytes. The stratum basale is also known to the person skilled in the art as stratum germinativum since it is the site of the generation of new keratinocytes by cell proliferation. The stratum germinativum is also the site where the epidermal stem cells are presumably located.

Due to its importance in disease, the study of the skin and, particularly, the epidermis has received considerable interest. However, in spite of extensive studies, testing of therapies for the treatment of skin diseases is currently cumbersome and expensive.

The explanatory power of animal experiments is limited by the considerable individual variation between different animals and by the differences between animal and human skin. Moreover, in the European Union animal models may not be used for the testing of cosmetic preparations, thus, creating a need for in vitro methods for toxicological analyses.

Consequently, various in-vitro models of human skin have been developed. Typically, three dimensional skin models comprise two layers, a dermal equivalent and an epidermal equivalent. The dermal equivalent comprises fibroblasts embedded in a matrix. This lower layer serves as an appropriate substratum for keratinocytes seeded on top to generate an epidermal equivalent. The formation of an epidermal equivalent by the keratinocytes critically depends on the support of the fibroblasts. Said fibroblasts require an external scaffold to attach to in order to perform their function. Numerous materials have been used to create scaffolds that closely resemble the natural surrounding encountered by fibroblasts in the dermis. Generally, approaches concentrate either on collagen-based preparations or on resorbable polymers such as poly(glycollic acid) or poly(vinyl alcohol) (see Auger et al., 2004, Biotechnol. Appl. Biochem., 39: 263-275 and Auxenfans et al., 2009, Eur. J. Dermatol., 2: 107-113).

The long-term stability of all of these models is inadequate. During cell culture, collagen as well as resorbable polymers are degraded by enzymes secreted by the fibroblasts. The scaffold, thus, slowly disintegrates. Consequently, the fibroblasts lack a mechanical support to attach to and lose their function. This in turn leaves the keratinocytes without stimulating cues from functional fibroblasts.

Thus, the problem underlying the present invention can be viewed as providing means and methods for improving the durability of in vitro skin models. The problem is solved by the embodiments described in the claims and the specification.

The present invention relates to a skin equivalent comprising
  a) a dermal equivalent comprising
    i. a matrix comprising a nonwoven viscose fabric and
    ii. fibroblasts; and
  b) keratinocytes.

The term skin equivalent refers to a three dimensional cell culture whose organization resembles the structure of the upper two layers of the skin (dermis and epidermis). Thus, the skin equivalent, preferably, comprises two layers. The lower layer, i.e. the dermal equivalent, comprises fibroblasts and a matrix. The upper layer comprises a layer of keratinocytes. In the present invention the upper layer of the skin equivalent is referred to as epidermal equivalent.

Furthermore, the skin equivalent, preferably, comprises a suitable culture medium for establishing and maintaining the skin equivalent. Preferably, the amount of culture medium in the vessel is at least in the later stages of the cultivation adjusted in such a way that the uppermost layer of the skin equivalent comprising the keratinocytes is not covered by the culture medium and exposed to the air. Thus, the situation of normal skin can be approximated in vitro.

Preferably, said suitable medium comprises FBS (fetal bovine serum) and/or L-ascorbic acid and/or an agent with an activity corresponding to TGFβ1. More preferably, the medium is based on Dulbecco's modified Eagle's Medium (DMEM). Preferably, the FBS is at a concentration of 5 to 20%, more preferably 7 to 15%, more preferably 8 to 12%, most preferably approximately 10%. Preferably, the L-ascorbic acid is present at a concentration of 5 to 500 μg/ml, more preferably 10 to 200 μg/ml, more preferably 20 to 100 μg/ml, more preferably 30 to 80 μg/ml, and most preferably approximately 50 μg/ml. Preferably the agent with the activity corresponding to TGFβ1 is present at a concentration corresponding to 0.2 to 5 ng/ml, more preferably 0.3 to 3 ng/ml, more preferably 0.5 to 2 ng/ml, more preferably 0.8 to 1.5 ng/ml, most preferably approximately 1 ng/ml of recombinant human TGFβ1. Preferably, the agent with an activity corresponding to TGFβ1 is TGFβ1, more preferably recombinant human TGFβ1.

The term "matrix" refers to the non-cellular, solid components of the dermal equivalent. These components provide the dermal equivalent with mechanical strength. In natural skin, fibroblasts produce components of the extracellular matrix and exert a tensile force on the fibrous macromolecular meshwork formed by them. Due to its mechanical strength, the extracellular matrix functions as a support and a structural scaffold for the fibroblasts. Only when their tensile force is countered by a stable support, fibroblasts display their natural pattern of growth and differentiation. Thus, the matrix of a dermal equivalent must have similar mechanical properties as the extracellular matrix in order to provide the fibroblasts with a suitable environment.

A matrix as referred to above, preferably, is a cellulose-based matrix. In particular, a nonwoven cellulose-based matrix is envisaged. Such a matrix may essentially consist of or comprise viscose or combinations thereof with polyester or other polymers. Rayon and viscose are used throughout this specification interchangeably. Suitable matrices shall serve as a scaffold for skin fibroblasts and allow for the generation of a skin equivalent but also allow for analysis of said sin equivalent by histological and/or biochemical techniques.

Therefore, the matrix material to be applied in accordance with the present invention, preferably, exhibits at least one of the following criteria:

(a) The matrix material can be sectioned and processed in histological applications;
(b) The matrix material can be sterilized for cell culture purposes, e.g., by autoclavation;
(c) The matrix material can serve as a scaffold for skin fibroblasts as specified elsewhere herein and the accompanying Examples below in more detail;
(d) The matrix material is biocompatible in that it is not toxic or otherwise harmful for the applied skin fibroblasts.

In the skin equivalent of the present invention the matrix, preferably, comprises an unwoven fabric made of viscose or rayon. The unwoven fabric, preferably, comprises fibres of uniform diameter. Preferably, said fibers are arranged in a three-dimensional scaffold structure wherein said structure allows for adhering of the fibroblasts within the said three-dimensional scaffold structure. The diameter of the dry fibres is, preferably, about 10 to 20 μm, more preferably, about 12 to 18 μm and, most preferably, about 14 to 16 μm. The diameter of the fibers is also dependent on the matrix material to be used. More preferably, a diameter of about 14 to 16 μm is envisaged for viscose or viscose polyester mixtures whereas a diameter of about 13 to 15 μm is envisaged for rayon. Preferably, the viscose is not modified by the introduction of further functional groups.

The thickness of the dry matrix is, preferably, about 0.2 mm to 1.0 mm, more preferably, about 0.3 mm to 1.0 mm and most preferably about 0.4 mm to 0.8 mm. It will be understood that the actual thickness of the matrix material used in the skin culture of the present invention may be variable and also influenced by swelling and loosening during handling measures. The appropriate thickness for a given skin equivalent depends on the features to be investigated. For example, studies on invasive growth behaviour of malignant keratinocytes or on vascularisation of the dermal equivalent or on extracellular matrix synthesis, assembly and remodelling require a larger dermal space provided by a thicker scaffold, whereas epidermal development and persistence is achieved with thinner scaffolds as well. The desired thickness is, preferably, adjusted by stacking various layers of matrix material and pressing them under heat. Ideally, this step is combined with sterilization by autoclaving. For regular skin models, a single layer of Jettex 2005/45 and 20010 can be, preferably, used, whereas SUNSORB® 300 and BEMCOT® M-3 shall be, preferably, applied in two layers.

Preferably, the matrix consists of material which can be autoclaved without changing its mechanical or chemical properties. Also preferably, the matrix is essentially free of binders or additives.

Particular preferred cellulose based materials and their properties are summarized in the following Table 1.

| Name | Composition | Fiber diameter (μm) ~ | Weight (g/m²) | Thickness = Caliper (μm) Average ~ | Company |
|---|---|---|---|---|---|
| Jettex 2005/45 | 100% Viscose | 16.5 | 45 | 480 | ORSA S.A. |
| Jettex 20010 | 100% Viscose | 16.2 | 100 | 750 | ORSA S.A |
| Jettex 4005 | 70% Viscose | 16.8 | 50 | 400 | ORSA S.A |
| SUNSORB® 300 | 30% Polyester 100% Rayon | 14.5 | 28.3 | 247 | BERKSHIRE ™ |
| BEMCOT® M-3 | 100% Rayon | 14.5 | 28 | 310 | Asahi Kasei Fibers Corporation |

In an especially preferred embodiment of the present invention, the matrix consists of a nonwoven fabric made of viscose and having properties as given below in table 2. Such a nonwoven viscose fabric is, for example, Jettex 2005/45 available from ORSA S.A., Italy.

TABLE 2

| Property | Value | Test Method |
|---|---|---|
| Weight | 45 g/m² ± 10% | ISO 9073.1 |
| Thickness | 0.48 ± 0.10 mm | ISO 9073.2 |
| Density | 94 g/dm³ | |

| | Longitudinal | Transversal | |
|---|---|---|---|
| Tensile trength | ≥6.0 daN | ≥1.4 daN | ISO 9073.3 |
| Extention at break | ≤60% | ≤130% | ISO 9073.3 |
| Tensile strength (wet) | ≥3.0 daN | ≥0.9 daN | ISO 9073.3 |
| Extention at break (wet) | ≤60% | ≤120% | ISO 9073.3 |
| Water absorptive capacity | ≥1000% | | EDANA 10.2-96/2 |
| Water absorptive time | ≤3 sec. | | EDANA 10.2-96/1 |
| Linting | ≤1.5 g/m² | | EDANA 300.0.84 |

Thus, more preferably, the matrix comprises a nonwoven viscose fabric having a weight of about 45 g/m²±10%, a thickness of about 0.48 mm±0.1 mm, a density of about 90 g/dm³ to about 100 g/dm³ and consisting of fibers having a diameter of about 10 to about 20 μm.

In another preferred embodiment, the matrix consists of a nonwoven rayon fabric having the properties recited in table 3, below. Such a matrix is available, e.g., as SUNSORB® 300 catalogue number SS300.0505.30 from BERKSHIRE™, US.

TABLE 3

| Property | |
|---|---|
| Basis weight | about 28.3 g/m² |
| Caliper | about 247 μm |
| Fibers | about 15 fibers/cm² (≥100 μm) |
| Particles | about 53 × 10³/cm² (≥0.5 μm) |
| Sorbency | about 352 mL/m² (capacity); about 12 mL/g (efficiency); about 2 sec. (rate) |

Thus, more preferably, the matrix comprises a nonwoven viscose fabric having a weight of about 28.3 g/m², a caliper of about 0.247 um, a fiber number of about 15 fibers/cm², a particle number of about 53×10³/cm², and a sorbency of about 352 mL/m2 (capacity), about 12 mL/g (efficiency) and a rate of about 2 seconds.

The term "about" as used herein refers to the precise values as indicated as well as to values which are within statistical variations or measuring inaccuracies. Preferably, such values are within the range of +15% to −15% of the precise value, more preferably, +10% to −10%, +5% to −5%, +2.5% to −2.5%, or +1% to −1% of the precise value.

The term "fibroblast" refers to a cell of mesenchymal origin. Fibroblasts are found in connective tissue. They secrete the building blocks of the extracellular matrix, i.e. collagens, glycosaminoglycans, reticular and elastic fibers and glycoproteins. Occasionally, the resting forms of fibroblasts are designated "fibrocytes". In the context of the present invention the term "fibroblast" refers to fibrocytes, i.e. resting fibroblasts, as well as to proliferating fibroblasts. In the context of the skin equivalent of the present invention fibroblasts function as feeder cells. They secrete nutrients and signalling molecules that are required for proper growth and maintenance of the keratinocytes. The fibroblasts in the skin equivalent of the present invention are, preferably, of human origin if the skin equivalent is designed to resemble human skin. If the skin model is designed to resemble the skin of another animal species, the fibroblasts originate, preferably, from this species.

The term "keratinocyte", preferably, refers to a cell which is found in the epidermis and produces keratin. In human beings, keratinocytes originate, mainly, from an interfollicular epidermal stem cells. In mice, stem cells located in the hair follicles are less important. These interfollicular epidermal stem cells are, preferably, characterized by their potential to retain cytoplasmic or nuclear labelling. This is presently the only reliable stem cell marker. In contrast to follicular stem cells, no truly specific marker protein could be identified for the interfollicular epidermal stem cells.

Advantageously, the skin equivalent of the present invention is suitable for the long term culture of skin equivalents. The skin equivalents known in the art rely on matrices made from collagen or absorbable polymers. The structure of these matrices is not stable because the material macerates. Moreover, the used materials are degraded by enzymes secreted by the cells of the skin equivalent. Therefore, the mechanical strength of the matrix which is vital for proper functioning of the fibroblasts is impaired and the dermal structure is destroyed. Thus, the life span of the skin equivalent is limited by the stability of the matrix. Typically, the life span of these skin equivalents does not exceed five weeks. The matrix of the present invention is more resistant against degradation, does not macerate and allows, therefore, a longer maintenance of skin equivalents. For many studies, e.g. on skin regeneration, wound healing, carcinogenesis or the long-term effects of chemical compounds on the skin, it is desirable to follow the development of a skin equivalent over a time of more than five weeks. Thus, the skin equivalent of the present invention is a valuable model system for the aforementioned studies. Furthermore, the matrix comprised by the dermal equivalent of the skin equivalent of the present invention has the right combination of rigidity and flexibility for the preparation of very thin sections. Thus, the skin equivalent of the present invention is more suitable to histological analysis. The skin equivalent of the present invention is also useful for studying aging processes and for identifying anti-aging agents, preferably, by applying the screening assays referred to elsewhere herein. The skin equivalent, in this context, is capable of reflecting skin of different ages. Thus, for the purposes of identifying a therapeutic agent or cosmetic agent that specifically has anti-aging properties on either the elderly or juvenile skin, the skin equivalent of the present invention is particularly well suited and useful.

In a preferred embodiment of the present invention, the matrix comprises collagen or collagen derivatives or fibrin gel in addition to the nonwoven viscose fabric. Hyaluronic acid derivatives (e.g. Lifecore's CORGEL™ BioHydrogel) are also preferred for the construction of a suitable gel matrix.

In a preferred embodiment of the present invention, the above described dermal equivalent further comprises endothelial cells. The term "endothelial cells" refers to those cells that line the interior surface of blood vessels. They are defined by specific surface markers, preferably, PECAM/CD31 and VEGF-receptors as well as typical cytoplasmatic proteins, preferably von Willebrand-factor, and by their potential to form multicellular tubular structures under adequate conditions.

The present invention, furthermore, relates to the use of a nonwoven viscose fabric, as described above for the manufacture of skin equivalents.

Moreover, the present invention relates to a method for manufacturing a skin equivalent comprising the steps of:
 a) providing a matrix comprising a nonwoven viscose fabric
 b) introducing fibroblasts into the matrix;
 c) seeding keratinocytes on top of the dermal equivalent; and
 d) culturing the skin equivalent.

The term "providing a matrix comprising nonwoven viscose fabric" refers to the provision of a matrix as described above. Preferably, the size and shape of the matrix are adapted to the size and shape of the skin equivalent to be manufactured. The matrix is, preferably, sterilized.

The fibroblasts are, preferably, introduced into the matrix as a fibrin gel suspension.

After introduction of the fibroblasts into the matrix, the dermal equivalent is, preferably, incubated for some time before adding the keratinocytes. More preferably, the incubation lasts a week. The dermal equivalent is, preferably, submersed in the culture medium.

After incubation of the dermal equivalent, keratinocytes are seeded on top of the dermal equivalent. Submersed cultivation of the skin equivalent is, preferably, continued for some time, more preferably for 24 hours. Finally, the amount of culture medium is, preferably, adjusted so that the surface of the skin equivalent is exposed to the air-medium interface.

During the culture of the skin equivalent, the culture medium is, preferably, changed every other day.

Preferably, the skin equivalent is cultured for a time sufficient to give rise to a skin equivalent which reflects a certain age of a natural skin. It has been found in accordance with the present invention that the skin equivalent in a culture ages comparable to natural skin and, thus, skin equivalents can be obtained by the aforementioned method of the present invention which reflect a certain age of the skin, e.g. elderly skin or juvenile skin. The skin age reflected by the skin equivalent can be determined by the person skilled in the art without further ado by monitoring biomarker expression or by monitoring histological processes.

In a preferred embodiment of the present invention, endothelial cells are introduced into the dermal equivalent prior to the seeding of keratinocytes.

Advantageously, a dermal equivalent comprising endothelial cells allows the formation of structures that resemble blood vessels. Thus, the skin equivalent of the present invention can be used to study angiogenesis in the skin in vitro.

Moreover, the present invention relates to a method for screening of agents capable of influencing skin comprising the steps of:
 a) contacting a skin equivalent according to the present invention with a candidate for an agent capable of influencing human skin; and b) determining whether the skin equivalent is influenced by the agent.

The term "method for screening of agents" refers to a method for determining whether a chemical compound or a physical stimulus is capable of changing the properties of the skin.

Chemical compounds are, preferably, peptides, nucleic acids or small molecules. In accordance with the present invention nucleic acids include DNA molecules, RNA molecules or derivatives thereof. DNA molecules are, preferably, oligonucleotides or polynucleotides such as cDNA or genomic DNA. RNA molecules, preferably, include microRNA, siRNA, mRNA, tRNA or ribozymes. Moreover, an agent as referred to in the present application is, preferably a bacterium or a virus.

A small molecule in accordance with the present invention is an organic or inorganic chemical compound. The small molecule may belong to any known chemical class of molecules. Usually, small molecules are lipids, fatty acids, purines, pyrimidines, alkaloids, amino acids, biogenic amines, isoprenoids or steroids. Peptides comprise, preferably, at least 3, at least 5 at least 10, at least 20 or at least 50 amino acids. Preferred physical stimuli are heat, radiation and mechanical stress. Radiation is, preferably, ionizing radiation such as UV light or nuclear radiation. Mechanical stress is, preferably, pressure or tension. It is, furthermore, envisaged by the present invention that any combination of more than one of the above described agents may be applied to the skin equivalent of the present invention.

The term "influencing the skin" refers to any change of the properties of the skin induced by the agents described above. Changes of the properties of the skin are, preferably, increased or decreased proliferation rates of any of the cells comprised by the skin equivalent, a changed pattern of cell differentiation of any of the cells comprised by the skin equivalent, a changed pattern of gene expression of any of the cells in the skin equivalent or changes of the genomic properties of any of the cells in the skin equivalent by insertions, deletions, epigenetic changes or point mutations. Preferably, the change of the properties of the skin which is caused by an agent is determined by comparing the properties of a skin equivalent exposed to said agent with the properties of a skin equivalent not exposed to said agent, i.e. a control.

Methods for determining the properties of a skin equivalent are well known in the art. Preferred methods are the histological examination of the skin equivalent, gene expression profiling with quantitative real-time PCR or hybridization-based methods such as DNA microarrays or the detection of genomic changes by PCR-based methods. Moreover, functional parameters can be evaluated. These are, preferably, transepidermal water loss and permeability for hydrophilic and hydrophobic substances as well as mechanical stiffness and elasticity of the skin equivalents as measures for the consolidation of dermis quality.

In a preferred embodiment of the present invention the skin equivalent is injured by cutting, burning and/or chaffing parts of the epidermal equivalent and/or the dermal equivalent. It is envisaged by the present invention that a combination of different agents and/or injuries can be applied to the skin equivalent of the present invention. Thus, it is possible to assess e.g. whether a chemical compound promotes wound healing or protects against the effects of UV light.

In another preferred embodiment of the present invention the agent to be screened is a therapeutic agent. A therapeutic agent is an agent that is capable of treating a disease or disorder. The term "treating" refers to ameliorating the diseases or disorders referred to herein or the symptoms accompanied therewith to a significant extent. Said treating as used herein also includes an entire restoration of the health with respect to the diseases or disorders referred to herein. It is to be understood that treating as used in accordance with the present invention may not be effective in all subjects to be treated. However, the term shall require that a statistically significant portion of subjects suffering from a disease or disorder referred to herein can be successfully treated. Whether a portion is statistically significant can be determined without further ado by the person skilled in the art using various well known statistic evaluation tools, e.g., determination of confidence intervals, p-value determination, Student's t-test, Mann-Whitney test etc. Preferred confidence intervals are at least 90%, at least 95%, at least 97%, at least 98% or at least 99%. The p-values are, preferably, 0.1, 0.05, 0.01, 0.005, or 0.0001. Preferably, the treatment shall be effective for at least 60%, at least 70%, at least 80%, or at least 90% of the subjects of a given cohort or population. Preferably, the therapeutic agent is substantially pure. More preferably, the therapeutic agent is an anti-aging agent that protects the skin from natural aging.

In yet another preferred embodiment of the present invention the agent to be screened is cosmetic agent. For the cosmetic agent, likewise, it is envisaged that the compound used in substantially pure form. Impurities, however, may be less critical than for a pharmaceutical composition. Preferably, the cosmetic agent is an anti-aging agent that protects the skin from natural aging.

It is to be understood that screening with respect to cosmetic as well as therapeutic agents refers to the screening for undesired effects, i.e. toxicity screening, as well as to the screening for beneficial effects, i.e. efficacy screening.

In yet another preferred embodiment of the method of the invention, a skin equivalent reflecting elderly or juvenile skin is applied.

Finally, in a preferred embodiment of the present invention the agent is tested for its capability of influencing epidermal stem cells. Preferred methods for determining whether epidermal stem cells are influenced by an agent are described above and disclosed in WO 2008/052963.

All references referred to above are herewith incorporated with respect to the specific disclosure content mentioned above and in their entirety.

FIGURES

FIG. 1: Microscopy at different magnifications (10× and 20×) of cryosections from skin equivalent cultures comprising skin fibroblasts using SUNSORB® 300 matrix in fibrin gel as a scaffold; (A) a single layer of the matrix at 10× magnification; (B) a single layer of matrix at 20× magnification; (C) matrix material structure of SUNSORB® 300 at 20× magnification in a skin equivalent.

Figure 2:
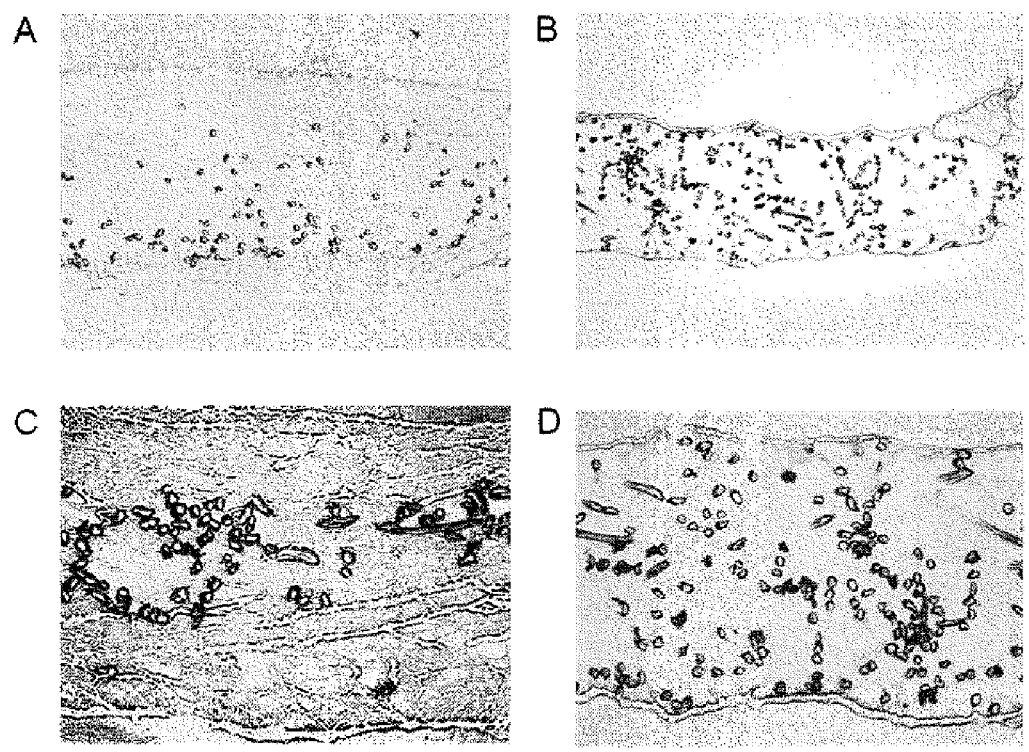

FIG. 2: Microscopy at different magnifications (10× and 20×) of cryosections from skin equivalent cultures comprising skin fibroblasts using BEMCOT® M-3 or Jettex 4005 matrix in fibrin gel as a scaffold; (A) a single layer of the matrix BEMCOT® M-3 at 10× magnification; (B) a single layer of matrix BEMCOT® M-3 at 20× magnification; (C) a single layer of the matrix Jettex 4005 at 10× magnification; (B) a single layer of matrix Jettex 4005 at 20× magnification.

The following examples are only meant to illustrate the present invention. They shall not limit the scope of the claims in any way.

EXAMPLES

Example 1

Generation of Skin Equivalents

The generation of the dermal part is the initial step in the production of skin equivalents as described here. Sterilized viscose scaffolds are transferred into cell culture membrane inserts (Becton-Dickinson cat. nr. 353093) with 2.3 cm diameter and 0.45 μm pores that have been placed in six-well culture plates.

Dermal fibroblasts cultivated in Dulbecco's MEM with 4 g glucose and 10% bovine fetal serum are trypsinized and suspended in fetal bovine serum at a density of $2\times10^6$ cells per ml. This suspension is mixed 1:1 with a thrombin solution containing 10 units per ml in PBS. 750 μl ml each of that mixture are applied onto the scaffolds in the membrane inserts. To these 750 μl of human fibrinogen dissolved in PBS, pH 7.0 without calcium and magnesium at a concentration of 10 mg per ml are added. Both liquids are mixed thoroughly by careful pipetting avoiding the generation of foam. When incubated at 37° C. the combined liquids form a fibrin gel consisting of 2.5 mg fibrinogen and 2.5 units thrombin per ml and comprising $7.5\times10^5$ fibroblasts (i.e. $1.8\times10^5$ per $cm^2$) together with the scaffold. These composite structures, the future dermal equivalents, are cultivated submerged in DMEM containing 10% fetal bovine serum 50 μg per ml ascorbic acid and 2 ng per ml TGFβ1 for two to seven days.

After this period, which is required to initiate the formation of authentic extracellular matrix, the culture medium is replaced with a mix of Ham's F12 and DMEM (1+3) containing 10% fetal bovine serum, $10^{-10}$ M cholera toxin, 50 μg ascorbic acid, 0.4 μg hydrocortisone and 500 units aprotinin per nil. The aprotinin supplementation is necessary to prevent the high fibrinolytic activity exerted by keratinocytes. The next day, glass rings (inner diameter 20 mm) are placed on the dermal equivalents to confine a central area onto which $10^6$ keratinocytes suspended in 1 ml of the above medium are seeded. After over night incubation to let the cells get settled the non adherent keratinocytes are carefully rinsed off, the medium is withdrawn and the membrane inserts with the skin equivalents are transferred into deep well-plates. Fresh medium of the above-mentioned composition but now with reduced aprotinin (200 units per ml) is filled in to a level that leaves the is epithelial surfaces of the cultures air-exposed. For further long-term cultivation under regular conditions (37° C., 95% humidity in air with 5% $CO_2$) the medium is changed every other day. To achieve long cultivation periods accurate aseptic handling of these skin equivalents is crucial.

Example 2

Analysis of Skin Equivalents

Skin equivalents produced and maintained according to the presented invention have a superior longevity compared to other state of the art skin models. With a life span of 10 weeks and more they outperform conventional models documented in literature or commercially distributed by the factor of 2 to 3 (Muffler et. al., 2008; Carlson, Alt-Holland, Egles, Garlick, 2008, Curr Prot Cell Biol; EPIDERM FT™, MatTek), with the option of prolonged cultivation periods physiological studies of tissue maturation processes become accessible.

Skin equivalents with SUNSORB® 300 (Berkshire, Inc. US), BEMCOT® M-3 (Asahi Kasei Fibers Corp, JP) or Jettex 4005 (ORSA S.A.) in fibrin gel were cultured for 2 weeks as specified in Example 1 and subsequently histologically analyzed. The skin equivalents were frozen and cryosectioned followed by microscopic analysis without mounting (see FIGS. 1 and 2).

As is evident from FIGS. 1 and 2, the nonwoven rayon matrices SUNSORB® 300 and BEMCOT® M-3 and the viscose polyester matrix Jettex 4005 gave comparable skin equivalent structures having even in part an intact epidermis.

The invention claimed is:

1. A skin equivalent comprising:
   (a) a dermal equivalent comprising a matrix comprising nonwoven viscose fabric and fibroblasts; and
   (b) keratinocytes;
wherein the nonwoven viscose fabric can be autoclaved without changing its mechanical or chemical properties.

2. The skin equivalent of claim 1, wherein the nonwoven viscose fabric comprises fibers of a uniform diameter of about 10 to about 20 μm.

3. The skin equivalent of claim 1, wherein the nonwoven viscose fabric has a thickness of about 0.2 to about 1.0 mm.

4. The skin equivalent of claim 1, wherein the dermal equivalent further comprises endothelial cells.

5. The skin equivalent of claim 1, wherein the nonwoven viscose fabric is essentially free of binders or additives.

6. The skin equivalent of claim 1, wherein the dermal equivalent of a) further comprises a fibrin gel.

7. The skin equivalent of claim 1, wherein the dermal equivalent forms a lower layer, and wherein the keratinocytes form an upper layer on top of the lower layer.

8. A method for manufacturing the skin equivalent of claim 1 comprising the steps of:
   (a) providing a dermal equivalent comprising a matrix comprising nonwoven viscose fabric;
   (b) introducing fibroblasts into the dermal equivalent;
   (c) seeding keratinocytes on top of the dermal equivalent; and
   (d) culturing the skin equivalent;
wherein the nonwoven viscose fabric can be autoclaved without changing its mechanical or chemical properties.

9. The method of claim 8, wherein endothelial cells are introduced into the dermal equivalent.

10. The method of claim 8, wherein the nonwoven viscose fabric comprises fibers of a uniform diameter of about 10 to about 20 μm.

11. The method of claim 8, wherein the nonwoven viscose fabric has a thickness of about 0.2 to about 1.0 mm.

\* \* \* \* \*